United States Patent [19]

Ruess et al.

[11] Patent Number: 4,886,824

[45] Date of Patent: Dec. 12, 1989

[54] COMPOSITIONS FOR CONTROLLING PLANT DISEASES AND THE USE THEREOF IN PLANT PROTECTION

[75] Inventors: Wilhelm Ruess, Pfeffingen; Pierre Urech, Wettingen; Jürg Eberle, Oberwil; Theodor Staub, Riehen, all of Switzerland

[73] Assignee: Ciba-Geigy Corporation, Ardsley, N.Y.

[21] Appl. No.: 215,103

[22] Filed: Jul. 5, 1988

Related U.S. Application Data

[63] Continuation-in-part of Ser. No. 891,935, Jul. 30, 1986, abandoned, which is a continuation of Ser. No. 722,420, Apr. 12, 1985, abandoned, which is a continuation of Ser. No. 499,061, May 27, 1983, abandoned.

[30] Foreign Application Priority Data

Jun. 8, 1982 [CH] Switzerland .................. 3528/82

[51] Int. Cl.$^4$ ................. A01N 43/38; A01N 43/64

[52] U.S. Cl. .................. 514/383; 514/417; 514/421

[58] Field of Search .............. 514/383, 417, 421

[56] References Cited

U.S. PATENT DOCUMENTS 4,598,085  7/1986  Heeres et al. ............... 514/383

OTHER PUBLICATIONS

The Merck Index, 10th Ed. (1983), pp. 244 & 603.

Primary Examiner—Allen J. Robinson
Attorney, Agent, or Firm—Bruce M. Collins; Edward McC. Roberts

[57] ABSTRACT

The invention relates to plant protection compositions based on a two-component system of plant fungicides, one of which is 1-[2-(2,4-dichlorophenyl)pentyl]-1H-1,2,4-triazole and the other is an N-haloalkanesulfenylphthalimide derivative.

In the range from 1:3 to 1:100 the disclosed mixtures display enhanced fungicidal activities.

11 Claims, No Drawings

COMPOSITIONS FOR CONTROLLING PLANT DISEASES AND THE USE THEREOF IN PLANT PROTECTION

CROSS-REFERENCE TO RELATED APPLICATIONS

This is a continuation in part of Ser. No. 891,935, filed on July 30, 1986, now abandoned, which is a continuation of Ser. No. 722,420, filed on Apr. 12, 1985, abandoned, which in turn is a continuation of Ser. No. 499,061, filed on May 27, 1983, abandoned.

The present invention relates to plant protection compositions based on a two-component system of plant fungicides. The interaction of the two active ingredients broadens the spectrum of activity and enhances the activity in a broad range of ratios of the two components.

The pesticidal combinations of this invention comprise 1-[2-(2,4-dichlorophenyl)pentyl]-1H-1,2,4-triazole of the formula

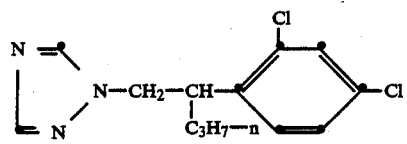

together with an N-haloalkanesulfenylphthalimide derivative of the formula II

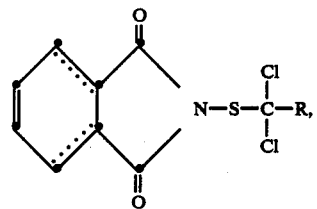

wherein each dotted line indicates a saturated carbon-carbon bond

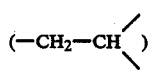

and R represents a chlorine atom or a —CHCl₂ group, or each dotted line indicates a carbon-carbon double bond

and R represents a chlorine atom.

The fungicidal compound of formula I is described in German Offenlegungsschrift 27 35 872 (which corresponds to GB-1,589,852).

The fungicidal compounds of formula II such as N-(trichlormethylthio)-1,2,3,6-tetrahydrophthalimide (hereinafter IIA) and N-(trichloromethylthio)phthalimide (hereinafter IIB) are described in U.S. Pat. Nos. 2,553,770; 2,553,771 and 2,553,776. The fungicidal compound N-(1,1,2,2-tetrachloroethylthio)-1,2,3,6-tetrahydrophthalimide (hereinafter IIC) is described in "Phytopathology" 1962, Vol. 52, pp. 754/755.

Combination formulations comprising active ingredients which belong to different chemical classes and producing potentiation of action in the control of phytopathogenic fungi are gaining importance as a result of the possibility thereby afforded of effectively counteracting the ever more frequently occurring resistance of these parasites to individual compounds. On the one hand, the increase in the fungicidally effective concentration necessitated by the resistance developed by the pests can be checked and even avoided or diminished. The resultant saving in pesticides has both economic as well as significant environmental advantages on account of the environmental impact. On the other hand, combination formulations have other advantages compared with single component formulations. For example, by broadening the activity spectrum, or resulting from the complementary activity spectra of the individual components, combination formulations are able to offer particular application advantages. Noxious fungi and related plant diseases, which usually occur concurrently, can be very effectively inhibited and eliminated in a single operation and at low rates of application. In addition, combination formulations afford advantages over single component formulations whenever higher rates of application are indispensable, e.g. in cases of severe attack or high risk of infestation. As a consequence of lowering the concentration of the individual components in ready-for-use mixture and of the concomitant diminution of undesirable, especially phytotoxic, side-effects, the user is provided with a combination formulation which, even under the unfavourable conditions imposed by increased risk of infestation, can be used easily and effectively against parasitic species of fungi and other plant diseases which occur concurrently, without first making time-consuming trial applications and, at the same time, without having to fear any impairment of the development of the crops.

A noxious fungus much feared in fruit growing is scab (Venturia spp.), which causes severe annual losses in important pome fruits, e.g. in apple and pear crops, and which is regarded worldwide as one of the worst pests of these fruits crops. Depending upon the vegetation state, the fungal infection can attack either or both the leaves and fruit. The fungal infection occurs worldwide but is particularly serious in regions with frequent rains during the early part of the growing season.

Up to now, efforts have been made to overcome this problem with conventional contact fungicides whose action is residual. However, it has been found that, the use of conventional contact fungicides is ineffective, particularly whenever the risk of infestation is severe, for example during periods of frequent rainfall or of warm, humid weather. Moreover, the fruit crops are attacked in as such weather conditions not only by scab, but also simultaneously by other parasitic and non-parasitic plant diseases such as powdery mildew, rust, storage diseases, physiological plant diseases such as lenticular rot, jonathan freckles etc., which diseases cause additional damage to the fruit and are insufficiently controlled by conventional antiscab agents.

Surprisingly, it has now been found that the systemic fungicide of formula I, which is highly effective against species of scab, mildew and rust fungi, but exhibits only slight activity against other plant diseases, in combination with the above contact fungicides of formula II which have a residual action, exhibits an unexpected potentiation of activity against scab fungi which significantly exceeds the simple sum of the antiscab action of the individual components and leads to a broadening of the activity spectrum. It is surprising that a lower concentration can be used while, within wide ranges of concentration, full effectiveness is retained. Further plant diseases, especially physiological diseases, are additionally controlled, resulting in an improvement in quality of the harvested crops.

A safer and more simplified protection of important crops of cultivated plants, e.g. apple, pear and cherry crops, is achieved by using the pesticidal combinations of this invention, and the increased effectiveness and activity spectrum significantly improve the quality of the harvested goods.

In addition, a very substantial reduction in environmental impact is achieved by lowering the concentration of active ingredient in the combination in the range from 30 to 60% as copared with the application of the individual components. The present invention permits control of the fungus without the need to apply large amounts of the antifungal agent.

Generally, the pesticidal combinations of the invention have for practical purposes a very advantageous broad fungicidal spectrum which encompasses the most important noxious fungi and other plant diseases which often occur concurrently, in particular physiological plant diseases such as lenticular rot or jonathan freckle (spot rot). They have very valuable curative, systemic and, in particular, preventative properties and can be used for protecting numerous cultivated plants. With the pesticidal combinations of this invention it is possible to inhibit or destroy the fungi which occur in plants or parts of plants (fruit, blossoms, leaves, stems, tubers, roots) in different crops of useful plants, while at the same time the parts of plants which grow later are also protected from attack by such noxious fungi. Fungicidal activity is observed for example against phytopathogenic fungi such as Fungi imperfecti (e.g. Helminthosporium, Septoria, Cercospora and Alternaria); Basidiomycetes (e.g. the genera Hemileia, Rhizoctonia, Puccinia); and in particular against fungi of the class of the Ascomycetes (e.g. Venturia, Podophaera, Erysiphe, Monilinia, Uncinula) especially Venturia species such as Venturia inaequalis, Venturia pirina and Venturia cerasi. In addition, systemic action is increased. They can also be used as seed dressing agents for protecting seeds (fruit, tubers, grains) and plant cuttings against fungus infections as well as against phytopathogenic fungi which occur in the soil.

Target crops to be protected within the scope of the present invention include cereals (wheat, barley, rye, oats, rice, sorghum and related crops), beet (sugar beet and fodder beet), drupes, soft fruit, and especially pomes (plums, peaches, almonds, cherries, strawberries, raspberries, gooseberries, currants, blackberries, and especially apples and pears) leguminous plants (beans, lentils, peas, soybeans), oil plants (rape, mustard, poppy, olives, sunflowers, coconuts, castor oil plants, cocoa beans, groundnuts), cucumber plants (cucumber, marrows, melons) fibre plants (cotton, flax, hemp, jute), citrus fruit (oranges, lemons, grapefruit, mandarins), vegetables (spinach, lettuce, asparagus, cabbages, carrots, onions, tomatoes, potatoes, paprika), lauraceae (avocados, cinnamon, camphor), or plants such as maize, tobacco, nuts, coffee, sugar cane, tea, vines, hops, bananas and natural rubber plants, as well as ornamentals (composites).

The pesticidal compositions of this invention are normally applied in the form of formulations suitable for application and can be applied to the crop area or plant to be treated, together with carriers, surfactants or application-promoting adjuvants customarily employed in the art of formulation. Suitable carriers and adjuvants may be solid or liquid and correspond to the substances ordinarily employed in formulation technology, e.g. natural or regenerated mineral substances, solvents, dispersants, wetting agents, tackifiers, binders or fertilisers.

A preferred method of applying the novel pesticidal compositions which contain at least one of said compounds, is foliar application. The number of applications and the rate of application depend on the risk of infestation by the corresponding pathogen (type of fungus). However, the combination formulations can also penetrate the plant through the roots via the soil (systemic action) by impregnating the locus of the plant with a liquid formulation, or by applying the substances in solid form to the soil, e.g. in granular form (soil application). The pesticidal compositions may also be applied to seeds (coating) by impregnating the seeds either with a liquid formulation or by coating them with a solid formulation.

The pesticidal compositions are used preferably together with the adjuvants conventionally employed in the art of formulation, and are therefore formulated in known manner to emulsifiable concentrates, coatable pastes, directly sprayable or dilutable solutions, dilute emulsions, wettable powders, soluble powders, dusts, granulates, and also encapsulations in e.g. polymer substances. Like the nature of the compositions, the methods of application, such as spraying, atomising, dusting, scattering or pouring, are chosen in accordance with the intended objectives and the prevailing circumstances.

The weight ratios of the compound of formula I to the compounds of formula II in the pesticidal combinations of this invention are in the range from 1:3 to 1:100. To bring about the synergistic effect, the ratio of 1:20 to 1:50 is regarded as advantageous and the ratio of 1:6 to 1:25 as being preferred. The rates of application of the pesticidal combinations are 4 to 100 g, preferably 25 to 75 g of active ingredient to 100 liters of spray mixture.

The formulations, i.e. the compositions containing the active ingredients and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol monomethyl or monoethyl ether, ketones such as cyclohexanone, strongly polar solvents such as N-methyl-2-pyrrolidone, dimethyl sulfoxide or dimethyl formamide, as well as epoxidised vegetable oils such as epoxidised coconut oil or soybean oil; or water.

The solid carriers used e.g. for dusts and dispersible powders, are normally natural fillers such as calcite, talcum, kaolin, 8ontmorillonite or attapulgite.

Depending on the nature of the pesticidal combination to be formulated, suitable surface-active compounds are nonionic, cationic and/or anionic surfactants having good emulsifying, dispersing and wetting properties. The term "surfactants" will also be understood as comprising mixtures of surfactants.

Suitable anionic surfactant can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or or natural fatty acid mixtures which can be obtained e.g. from coconut oil or tallow oil. Mention may also be made of fatty acid methyltaurin salts.

More frequently, however, so-called synthetic surfactants are used, especially fatty sulfonates, fatty sulfates, sulfonated benzimidazole derivatives or alkylarylsulfonates.

Non-ionic surfactants are preferably polyglycol ether derivatives of aliphatic or cycloaliphatic alcohols, or saturated or unsaturated fatty acids and alkylphenos, said derivatives containing 3 to 30 glycol eher groups and 8 to 20 carbon atoms in the (aliphatic) hydrocarbon moiety and 6 to 18 carbon atoms in the alkyl moiety of the alkylphenols.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxyethoxyethanol. Fatty acid esters of polyoxyethylene sorbitan and polyoxyethylene sorbitan trioleate are also suitable non-ionic surfactants.

Cationic surfactants are preferably quaternary ammonium salts which contain, as N-substituent, at least one $C_8$–$C_{22}$alkyl radical and, as further substituents, lower unsubstituted or halogenated alkyl, benzyl or lower hydroxyalkyl radicals.

The surfactants customarily employed in the art of formulation are described e.g. in "Mc Cutcheon's Detergents and Emulsifiers Annual", MC Publishing Corp. Ridgewood, N.J., 1979, and Sisley and Wood, "Encyclopedia of Surface Active Agents", Chemical Publishing Co., Inc. New York, 1980.

The agrochemical formulations usually contain 0.1 to 99%, preferably 0.1 to 95%, of the mixture of compounds of formula I and II, plus 1 to 99.9%, preferably 99.8 to 5%, of solid or liquid adjuvant, and 0 to 25%, preferably 0.1 to 25%, of a surfactant.

Whereas commercial products are preferably formulated as concentrates, the end user will normally employ dilute formulations.

The formulations may also contain further ingredients, such as stabilisers, antifoams, viscosity regulators, binder, tackifiers as well as fertilisers or other active ingredients in order to obtain special effects.

Such agrochemical formulations also constitute an object of the present invention.

A number of formulations are set forth below by way of illustration, without implying any restriction to the invention.

FORMULATION EXAMPLES (throughout, percentages are by weight)

| Wettable powders | (a) | (b) | (c) |
|---|---|---|---|
| a combination of I and II | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| octylphenol polyethylene glycol ether (7-8 moles of ethylene oxide) | — | 2% | — |
| highly dispersed silicic acid | 5% | 10% | 10% |
| kaolin | 62% | 27% | — |

The active ingredients are thoroughly mixed with the adjuvants and the mixture is thoroughly ground in a suitable mill, affording wettable powders which can be diluted with water to give suspensions of the desired concentrations.

| Emulsifiable concentrate | |
|---|---|
| a combination of I and II | 10% |
| octylphenol polyethylene glycol ether (4-5 moles of ethylene oxide) | 3% |
| calcium dodecylbenzenesulfonate | 3% |
| castor oil polyglykol ether (36 moles of ethylene oxide) | 4% |
| cyclohexane | 30% |
| xylene mixture | 50% |

Emulsions of any required concentration can be obtained from this concentrate by dilution with water.

| Dusts | (a) | (b) |
|---|---|---|
| a combination of I and II | 5% | 8% |
| talcum | 95% | — |
| kaolin | — | 92% |

Ready-for-use dusts are obtained by mixing the active ingredients with the carriers, and grinding the mixture in a suitable mill.

| Extruder granulate | |
|---|---|
| a combination of I and II | 10% |
| sodium lignosulfonate | 2% |
| carboxymethylcellulose | 1% |
| kaolin | 87% |

The active ingredient is mixed and ground with the adjuvants, and the mixture is subsequently moistened with water. The mixture is extruded and then dried in a stream of air.

| Coated granulate | |
|---|---|
| a combination of I and II | 3% |
| polyethylen glycol 200 | 3% |
| kaolin | 94% |

The finely ground active ingredients are uniformly applied, in a mixer, to the kaolin moistened with polyethylene glycol. Non-dusty coated granulates are obtained in this manner.

| Suspension concentrate | |
|---|---|
| a combination of I and II | 40% |
| ethylene glycol | 10% |
| nonylphenol polyethylene glycol (15 moles of ethylene oxide) | 6% |
| sodium ligninsulfonate | 10% |

| Suspension concentrate | |
|---|---|
| carboxymethylcellulose | 1% |
| 37% aqueous formaldehyde solution | 0.2% |
| silicone oil in the form of a 75% aqueous emulsion | 0.8% |
| water | 32% |

The finely ground active ingredients are intimately mixed with the adjuvants, giving a suspension concentrate from which suspensions of any desired concentration can be obtained by dilution with water.

BIOLOGICAL EXAMPLES

The increased effectiveness of compositions of the invention is demonstrated by means of the combinations tested in the biological tests described below.

Potentiation is always present if the fungicidal action of the combination is greater than the expected action.

The expected action E for a given combination, e.g. of two fungicides, is expressed by the so-called Colby formula (used originally only to determine the expected value E of mixtures of herbicides) and can be calculated as follows (cf. Colby, S. R., Calculating synergistic responses and antagonistic responses of herbicide combinations, Weeds 15, pp. 20–22. Limpel et al., 1062 "Weeds control by . . . certain combinations", Proc. NEWCL, Vol. 16, pp. 48–53): (g a.i./hl=gram of active ingredient per hectoliter of spray mixture)

$X$ = percentage action of fungicide I at a rate of application of p gram of a.i./hl $Y$ = percentage action of fungicide II at a rate of application of q gram of a.i./hl $E$ = the expected action of fungicide I+II at a rate of application of p+q gram of a.i./hl then according to Colby: $E = X + Y - X \cdot Y / 100$ If the actually observed action (O) is greater than that calculated and expected (=E), then the action of the combination is greater than the additive action, i.e. there is potentiation. In the following Examples, E has been calculated in accordance with the above equation.

EXAMPLE 1

Action against *Venturia inaequalis* on apples 10 apple seedlings of the McIntosh variety are reared in 5 cm plastic pots and, when in the 7- to 9-leaf stage, are sprayed just short of dripping wet with 5 ml of a spray mixture prepared from a wettable powder formulation of one of the pesticides or with a combination thereof (see Table hereunder). The treated plants are infected 24 hours later with a conidia suspension (300,000 conidia spores/ml) of Venturia inaequalis at 22° C. The test plants are then stood in a greenhouse for another 22 days at 20°–22° C. Evaluation of the test is made on the 15th and 20th day after inoculation by measuring the leaf area attacked by the fungus on the two most recently inoculated leaves and expressing it as a percentage of their total leaf area.

RESULTS OBTAINED IN EXAMPLE 1

Crop: apple
Variety: McIntosh
Disease: apple scab (*Venturia inaequalis*)

| Rate of application in g of a.i./100 litres | | | Action against apple scab (%) | |
|---|---|---|---|---|
| compound I | compound IIA | ratio | E (expected, i.e. additive action) | O (observed) |
| 2.5 | 0 | | N/A | 71 |
| 2 | 0 | | N/A | 55 |
| 1.5 | 0 | | N/A | 42 |
| 1 | 0 | | N/A | 19 |
| 0 | 50 | | N/A | 91 |
| 0 | 25 | | N/A | 83 |
| 0 | 12 | | N/A | 51 |
| 0 | 6 | | N/A | 38 |
| 2.5 | 50 | 1:20 | 97** | 98* |
| 2 | 25 | 2:25 | 92 | 98* |
| 2 | 12 | 1:6 | 78 | 86* |
| 1 | 25 | 1:25 | 86 | 99* |
| 1 | 12 | 1:12 | 60 | 82* |
| 0 | 0 | | 100% attack | 100% attack |

N/A = not applicable
*potentiation
**In ranges approaching 100% it is difficult to recognize potentiation

EXAMPLE 2

Action against leaf and fruit scab on apples
(Field trial in Canton Valais, Switzerland)
Crop: apple trees, Golden Delicious variety
Trial: 3 trees per parcel, 11-year-old, 3 repeats
Application dates: from May 13 to September 8 at intervals of 7–12 days, 12 spray applications
Periods of scab infestation (natural infestation): continuous infestation from May to October.
Test evaluation: June 9: Leaves with scab infestation (%), (100 leaves per tree); October 23: Fruit with scab infestation (%), (<100 fruit assessed per tree).

| Rate of application in g of a.i./100 litres | | | Results | | | |
|---|---|---|---|---|---|---|
| | | | Action against leaf scab (%) | | Action against fruit scab (%) | |
| compound I | compound IIA | ratio | E | O | E | O |
| 2.5 | 0 | | | 71 | | 68 |
| 0 | 47.5 | | | 71 | | 35 |
| 2.5 | 47.5 | 1:19 | 93 | 98* | 79 | 98* |
| 0 | 0 | | (100% attack) | | (100% attack) | |

*potentiation

EXAMPLE 3

Action against leaf and fruit scab on apples
(Field trial in Canton Valais, Switzerland)
Crop: apple trees, Idared variety
Trial: 3 trees per parcel, 11-year-old, 3 repeats
Application dates: from April 7 to September 16 at intervals of 7–13 days, 16 spray applications
Periods of scab infestation (natural infestation): continuous infestation from May to October.
Test evaluation: August 7: Leaves with scab infestation (%), (100 leaves per tree); October 14: Fruit with scab infestation (%), (100 fruit per tree).

| Rate of application in g of a.i./100 liters | | | Results | | | |
|---|---|---|---|---|---|---|
| | | | Action against leaf scab (%) | | Action against fruit scab (%) | |
| compound I | compound IIA | ratio | E | O | E | O |
| 2.5 | 0 | | N/A | 38 | N/A | 30 |

-continued

| Rate of application in g of a.i./100 liters | | Results ratio | Action against leaf scab (%) | | Action against fruit scab (%) | |
|---|---|---|---|---|---|---|
| | | | E | O | E | O |
| 0 | 47.5 | | N/A | 35 | N/A | 60 |
| 2.5 compound I | 47.5 compound IIB | 1:19 | 60 | 73* | 72 | 90* |
| 2.5 | 0 | | N/A | 38 | N/A | 30 |
| 0 | 47.5 | | N/A | 27 | N/A | 78 |
| 2.5 | 47.5 | 1:19 | 55 | 81* | 84 | 94* |
| 0 | 0 | | (100% attack) | | (100% attack) | |

*potentiation

EXAMPLE 4

Greenhouse tests against *Venturia inaequalis*

Ten apple seedlings of the McIntosh variety are reared in 5 cm plastic pots and, when in the 6- to 8-leaf stage, are sprayed just short of dripping wet with 5 ml of a wettable powder formulation of the test composition. The treated plants are infected 24 hours later with a conidia suspension (190,000 conidia spores/ml) of *Venturia inaequalis* at 22° C. The test plants then are allowed to stand in a greenhouse for an additional 22 days at 20° C. to 25° C. Evaluation of the tests is made on the 15th day after inoculation by measuring the leaf area attacked by the fungus on the most recently inoculated leaves which area is expressed as a percentage of the total leaf area. untreated but infected plants serve as "untreated controls" (Venturia infestation being 100% attack).

| Rate of Application (g/100 liters) | | Results | Action against *Venturia inaequalis* | |
|---|---|---|---|---|
| I | IIA | Ratio | Expected | Observed |
| 0 | 0 | N/A | N/A | 0 |
| 1.0 | 0 | N/A | N/A | 19 |
| 0 | 12 | N/A | N/A | 51 |
| 1.0 | 12 | 1:12 | 60 | 82* |
| 1.0 | 25 | 1:25 | 86 | 99* |
| 2.0 | 0 | N/A | N/A | 55 |
| 2.0 | 12 | 1:6 | 78 | 86* |
| 2.0 | 25 | 1:12 | 92 | 98* |
| 2.5 | 0 | N/A | N/A | 71 |
| 2.5 | 50 | 1:20 | 97 | 98* |

*potentiation

EXAMPLE 5

Field test against *Venturia inaequalis*

Field tests were carried out in Montesanto, in the area of Ferrara, Italy, using a crop of 8-year-old apple trees of the Starking Delicious variety. One tree on each of four randomized parcels was treated. The trees selected were sprayed dripping wet with a wettable powder formulation of test compositions. Six spray applications were employed over a period of six weeks in April and May at intervals of 7 days.

Evaluation was made by measuring the leaf area attacked by the fungus on 100 leaves per tree having scab infestation and expressing it as a percentage of their total leaf area. Untreated but infested plants served as untreated controls, *Venturia inaequalis* infestation thereon being equivalent to 100% attack.

| Rate of Application (g/100 liters) | | Results | Action against *Venturia inaequalis* | |
|---|---|---|---|---|
| I | IIB | Ratio | Expected | Observed |
| 0 | 0 | N/A | N/A | 0 |
| 2.5 | 0 | N/A | N/A | 82 |
| 0 | 25 | N/A | N/A | 54 |
| 2.5 | 25 | 1:10 | 91 | 100* |
| 0 | 50 | N/A | N/A | 79 |
| 2.5 | 50 | 1:20 | 96 | 100* |

*potentiation

EXAMPLE 6

Greenhouse test against *Venturia inaequalis*

Ten apple seedlings of the McIntosh variety were submitted to the same test method as described in Example 4.

| Rate of Application (g/100 liters) | | Results | Action against *Venturia inaequalis* | |
|---|---|---|---|---|
| I | IIC | Ratio | Expected | Observed |
| 0 | 0 | N/A | N/A | 0 |
| 0.5 | 0 | N/A | N/A | 1 |
| 0 | 3 | N/A | N/A | 66 |
| 0.5 | 3 | 1:6 | 66 | 90* |
| 0 | 6 | N/A | N/A | 72 |
| 0.5 | 6 | 1:12 | 72 | 91* |
| 0 | 12 | N/A | N/A | 57 |
| 0.5 | 12 | 1:24 | 57 | 94* |

*potentiation

What we claim is:

1. A composition for controlling fungal diseases in agriculture and horticulture comprising a fungicidally effective amount of a mixture of
   (a) 1-[2-(2,4-dichlorophenyl)pentyl]-1H-1,2,4,-triazole (compound I) and
   (b) an N-haloalkanesulfenylphthalimide derivative of the formula II

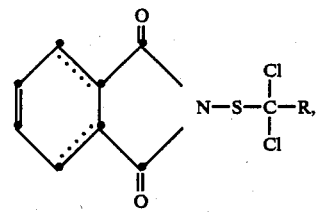

wherein each dotted line indicates a saturated carbon-carbon bond and R represents a chlorine atom or a —CHCl$_2$ group, or wherein each dotted line indicates a carbon-carbon double bond and R represents a chlorine atom, the weight ratio of said compound I to said compound II being from 1:3 to 1:100, in combination with a solid or liquid carrier wherein the amount of compound I is sufficient to potentiate the fungicidal activity of said phthalimide compound.

2. The composition according to claim 1 wherein the weight ratio of said compound I to said compund II is from 1:6 to 1:25.

3. The composition according to claim 1 wherein the compound of formula II is N-(trichloromethylthio)-1,2,3,6-tetrahydrophthalimide.

4. The composition according to claim 1 wherein the compound of formula II is N-(trichloromethylthio)-phthalimide.

5. The composition according to claim 1 wherein the compound of formula II is N-(1,1,2,2-tetrachloroethylthio)-1,2,3,6-tetrahydrophthalimide.

6. A method of controlling fungal diseases in agriculture and horticulture which comprises applying to the plants or their locus a fungicidally effective amount of a mixture of
(a) 1-[2-(2,4-dichlorophenyl)pentyl]-1H-1,2,4,-triazole (compound I) and
(b) an N-haloalkanesulfenylphthalimide derivative of the formula II

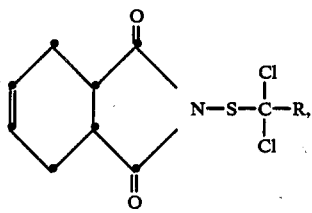

wherein each dotted line indicates a saturated carbon-carbon bond and R represents a chlorine atom or a —CHCl$_2$ group, or wherein each dotted line indicates a carbon-carbon double bond and R represents a chlorine atom, the weight ratio of said compound I to said compound II in the mixture being from 1:3 to 1:100, in combination with a solid or liquid carrier wherein the amount of compound I is sufficient to potentiate the fungicidal activity of said phthalimide compound.

7. The method according to claim 6 wherein the weight ratio of said compound I to said compound II being from 1:6 to 1:25.

8. The method according to claim 6 wherein the compound of formula II is N-(trichloromethylthio)-1,2,3,6-tetrahydrophthalimide.

9. The method according to claim 6 wherein the compound of formula II is N-(trichloromethylthio)-phthalimide.

10. The method according to claim 6 wherein the compound of formula II is N-(1,1,2,2-tetrachloroethylthio)-1,2,3,6-tetrahydrophthalimide.

11. The method according to claim 6 wherein said disease is caused by a Venturia fungus.

* * * * *